United States Patent [19]

Sarin et al.

[11] Patent Number: 5,302,581
[45] Date of Patent: Apr. 12, 1994

[54] PULMONARY SURFACTANT PROTEIN FRAGMENTS

[75] Inventors: Virender K. Sarin, Libertyville; Jack L. Fox, Lake Bluff; Shanker L. Gupta, Vernon Hills, all of Ill.; Darryl R. Absolom, Columbus, Ohio

[73] Assignee: Abbott Laboratories, Abbott Park, Ill.

[21] Appl. No.: 826,323

[22] Filed: Jan. 22, 1992

Related U.S. Application Data

[62] Division of Ser. No. 397,151, Aug. 22, 1989, Pat. No. 5,238,920.

[51] Int. Cl.$^5$ ............... A61K 37/02; C07K 7/08; C07K 7/10
[52] U.S. Cl. .................. 514/12; 514/8; 514/13; 530/324; 530/325; 530/326
[58] Field of Search .............. 530/324, 325, 326; 514/8, 12, 13

[56] References Cited

U.S. PATENT DOCUMENTS 5,164,369  11/1992  Cochrane et al. ............... 514/12

FOREIGN PATENT DOCUMENTS

| 307513 | 3/1989 | European Pat. Off. | 514/12 |
| 335133 | 10/1989 | European Pat. Off. | 514/12 |
| WO87/02037 | 4/1987 | World Int. Prop. O. | 514/12 |
| WO89/00167 | 1/1989 | World Int. Prop. O. | 514/12 |
| WO89/06657 | 7/1989 | World Int. Prop. O. | 530/324 |

OTHER PUBLICATIONS

Chemical Abstracts, vol. 112, 1990, p. 526, Abstract No. 136888J, Columbus, Ohio, U.S.A.
JP-A-01121299, Dec. 5, 1989.

*Primary Examiner*—Lester L. Lee
*Attorney, Agent, or Firm*—Donald O. Nickey

[57] ABSTRACT

This invention discloses that certain fragments of a pulmonary surfactant protein exhibit unexpected surface activity. These protein fragments are useful in preparing formulations for the treatment of respiratory disease.

18 Claims, No Drawings

PULMONARY SURFACTANT PROTEIN FRAGMENTS

This is a division of application Ser. No. 07/397,151, filed on Aug. 22, 1989, now U.S. Pat. No. 5,238,920.

TECHNICAL FIELD This invention relates to novel polypeptides and the use of these peptides in the preparation of formulations for the treatment of respiratory disease.

BACKGROUND OF THE INVENTION

The present invention relates to novel compositions of matter and methods for the treatment of respiratory distress with these novel compositions. This invention also relates to the use of polypeptides (protein fragments) which enhance the surfactant-like properties of phospholipids. More specifically, the present invention relates to novel polypeptides comprising fragment replicas and analogs of fragment replicas of the naturally occurring low molecular weight hydrophobic surfactant associated protein known as SP-B and to their use in the formulation of novel medicaments useful in the establishment, modification and/or maintenance of pulmonary surface tension.

Incorporated herein by reference is U.S. Pat. No. 4,659,805 which discloses and claims a high molecular weight surfactant protein known as SP-A.

The prior art discloses the discovery, method of isolation, characterization and use of a family of naturally occurring mammalian surfactant-associated proteins. Members of this family have been designated as SP-A, SP-B and SP-C. These proteins are known to have the capacity to effect the surfactant-like activity of both natural and synthetic phospholipids. It should be noted that the associated scientific literature also uses the nomenclature of SAP-B, SAP-(Phe), SAP-6 (Phe), and SPL-(Phe) for SP-B. SP-C is also referred to as SAP-C, SAP-(Val), SAP-6 (Val) and SPL (Val) in the prior art. These two proteins (SP-B and SP-C) are distinct gene products with unique amino acid sequences. Both proteins are derived from proteolytic processing of larger precursor proteins synthesized by pulmonary type II epithelial cells.

SP-B is generated by cleavage of the precursor protein at a glutamine-phenylalanine peptide bond resulting in the naturally occurring protein having 78 amino acid residues, with an N-terminal residue of phenylalanine and a simple molecular weight of about 8,700. SP-B isolated from human lung migrates on polyacrylamide gels as an entity having a relative molecular weight ($M_r$) of 7–8,000 after sulfhydryl reduction. Without sulfhydryl reduction the naturally occurring protein is also found as large oligomers. SP-B is extremely hydrophobic, a physical property which is consistent with its in vivo strong association with phospholipids and solubility in organic solvents such as chloroform and methanol.

SP-C has an amino terminal glycine residue, a molecular weight of about 3,700, a polyvaline sequence, and, like SP-B, is also extremely hydrophobic. In addition, both proteins (SP-B and SP-C) are substantially resistant to enzyme degradation by proteases (trypsin, chymotrypsin and staphylococcus nucleotide V-8), endoglycosidase F, and collagenase. Neither SP-B nor SP-C exhibits any degradation or alteration in their molecular weight distribution following treatment with these enzymes. In this behavior, as well as on the basis of amino acid sequence information, the proteins are clearly different from the more hydrophilic and higher molecular weight protein SP-A (also known as SAP-35).

SP-A is present in natural lung surfactant material and has a reduced molecular weight of 30–36,000. SP-A is a glycoprotein containing an internal collagen-like region which is rich in glycine and hydroxyproline. This protein has a N-linked complex carbohydrate and a calcium binding site in the C-terminal globular domain. SP-A is known to bind to phospholipids and is thought to confer important structural organization to the surfactant lipids. This protein is also believed to play a role in preventing the inhibition of pulmonary surfactant activity by plasma or other proteins.

The complete amino acid sequence of SP-B and SP-C has been determined from amino acid analysis and deduced from cDNA's derived from the mRNA's encoding the proteins. The SP-B and SP-C proteins are available as isolates from natural sources, such as bronchioalveolar lung washes and minced lung tissue or as products resulting from the application of recombinant DNA methodologies. When formulated with phospholipids (including synthetic phospholipids) these proteins provide compositions useful in the treatment of pulmonary disorders.

As is often the case with biologically active substances, the isolation of substantial quantities of hydrophobic SP-B and SP-C proteins from natural sources is expensive and labor intensive. Likewise, production of these proteins by recombinant DNA techniques requires substantial effort in terms of design and achieving optimal host/vector expression systems to facilitate production of the proteins. In addition, considerable effort is required to develop effective isolation strategies to separate and purify the expressed protein of interest from the unwanted material. With respect to the specific case of SP-B, the low molecular weight, extreme hydrophobicity and large number of cysteine residues markedly complicates commercial development of efficient expression and/or isolation procedures.

Due to these problems commercial production of SP-B via isolation from natural materials or expression of the protein via recombinant DNA strategies is difficult. The medical community has a need for commercial quantities of SP-B and the present invention fulfills that need through the discovery that only a portion of the SP-B protein molecule is required for the formulation of an effective pulmonary surfactant.

The usefulness of the naturally occurring SP-B and SP-C proteins resides in their ability to significantly improve the surface tension lowering capacity and respreadability of phospholipid admixtures. Natural SP-B and SP-C have been shown, both individually as well as in combination, to facilitate this improvement in surfactant-like activity of phospholipids. However, what has not previously been established is whether the entire protein sequence is necessary to achieve this optimum condition or whether only certain regions or fragments of these proteins, either alone or in certain combinations, might achieve the same result. The prior art fails to suggest, disclose or contemplate the instant discovery. Further one skilled in the art can not a priori determine what fragments will evidence utility or that certain fragments will have activity exceeding that of the complete natural protein.

It is clear that synthesis of replica fragments, or analogs thereof, would provide numerous advantages over the chemical or recombinant synthesis of the entire sequence. These advantages include cost, ease of production, isolation and purification.

DISCLOSURE OF THE INVENTION

There is disclosed a composition of matter which comprises at least one fragment of the SP-B protein which exhibits surfactant activity when admixed with phospholipids, said fragment being that portion of the SP-B protein which contains at least a terminal amino acid sequence and substitution, deletion and addition analogs thereof.

There is also disclosed a composition of matter comprising said SP-B fragments or analogs thereof in combination with at least one lipid. The lipid is selected from the group consisting of synthetic phospholipids, naturally occurring phospholipids, neutral lipids, cholesterol, cholesterol esters, phosphatidylcholine, disaturated phosphatidylycholine, phosphatidylglycerol, dipalmitoyl phosphatidylcholine, phosphatidylinositol and mixtures thereof.

The most preferred lipids are a mixture comprising dipalmitoyl-sn-phosphatidylcholine (DPPC), egg phosphatidylglycerol (PG) and palmitic acid (PA).

Also disclosed is a method for the treatment of pulmonary surfactant deficient states (e.g. hyaline membrane disease) and/or abnormal surfactant states (e.g. respiratory distress syndrome), said method comprising administration of an effective amount of a surfactant composition to a patient in need of treatment, said surfactant composition consists of at least one SP-B fragment, said fragment contains at least a terminal amino acid sequence; and at least one lipid.

Further disclosed is a method for pulmonary drug delivery, said method consisting of administering to a patient in need, a therapeutically effective amount of a composition comprising: 1) a fragment of the SP-B protein that contains at least a terminal amino acid sequence; 2) at least one lipid; and 3) an appropriate therapeutic agent.

Also disclosed is a method for the preparation of polyclonal and monoclonal antibodies exhibiting specificity for the antigenic determinants on natural SP-B, said method comprising immunizing with an effective amount of a composition comprising at least one fragment of the SP-B protein, said fragment being that portion of the SP-B protein which contains at least a terminal amino acid sequence and substitution, deletion, replicate and addition analogs thereof; with suitable carriers and/or adjuvants.

According to the present invention, novel, non-naturally occurring synthetic peptides are disclosed which combined with of two or more SP-B analog replicas, and/or combinations of one or more SP-B analog replicas with natural, synthetic or recombinant SP-C and/or SP-A. The polypeptide fragments of the invention are readily and economically synthesized via chemical or recombinant technologies and may be formulated with natural or synthetic phospholipids to yield admixtures which exhibit markedly enhanced surfactant-like activity as compared to the phospholipid mixtures alone.

BEST MODE FOR CARRYING OUT THE INVENTION

A number of polypeptides of various lengths and corresponding to various regions of the natural SP-B protein were synthesized by means of solid phase peptide synthesis. However, identical and/or similar fragments could also be produced by known recombinant DNA methods. This invention contemplates that the various SP-B fragments can be produced using recombinant technologies and that one skilled in the art of recombinant synthesis will appreciate that fragments of certain size (length of amino acid sequence) will be more readily produced via this technology. Thus, the scope of this invention is intended to include all SP-B fragments that contain a terminal amino acid sequence which exhibit surfactant activity and which can be facilely produced using recombinant technologies.

Table 1 sets forth the molecular mass, position, and number of amino acids constituting the various synthesized SP-B fragments and the associated nomenclature for the purposes of this application.

TABLE 1

Description of the Nomenclature, Molecular Mass, Position and Number of Amino Acid Residues of Synthesized SP-B Peptide Fragments

| Nomenclature | Molecular Mass | Position | # of Amino Acids |
|---|---|---|---|
| SP-B(1-78) | 8663.4 | 1-78 | 78 (complete protein) |
| SP-B(1-20) | 2402.1 | 1-20 | 20 |
| SPB(1-40) | 4504.9 | 1-40 | 40 |
| SP-B(1-60) | 6611.6 | 1-60 | 60 |
| SP-B(30-60) | 3261.1 | 30-60 | 30 |
| SP-B(12-60) | 5277.8 | 12-60 | 49 |
| SP-B(27-78) | 5682.4 | 27-78 | 52 |
| SP-B(53-78) | 2975.9 | 53-78 | 26 |

As the result of formulation experiments and testing (as hereinafter described) the inventors have determined that certain of these fragments exhibit the unexpected, unpredicted, unusual and surprising ability to facilitate enhanced surface activity of phospholipid admixtures.

The most preferred polypeptides of the invention include:

(a) SP-B (1-20) having the amino acid sequence:

NH$_2$—Phe—Pro—Ile—Pro—Leu—Pro—Tyr—Cys—Trp—Leu—Cys—Arg—Ala—Leu—Ile—Lys—
1                                                                                              10

Arg—Ile—Gln—Ala—OH
20 have the ability to markedly enhance the surfactant-like activity of natural and/or synthetic phospholipids. The synthetic polypeptides of this invention comprise replicas of portions (fragments) of the known continuous amino acid sequences of naturally occurring SP-B, which may be combined with phospholipids alone, or which is seen to constitute a replica of the initial 20, amino terminal, amino acid residues of the SP-B protein; and (b) SP-B (53-78) having the amino acid sequence:

NH₂—Tyr—Ser—Val—Ile—Leu—Leu—Asp—Thr—Leu—Leu—Gly—Arg—Met—Leu—Pro—Gln—
       53                                  60

Leu—Val—Cys—Arg—Leu—Val—Leu—Arg—Cys—Ser—OH
      70                              78 which is seen to constitute a replica of the final 26, carboxyl terminal, amino acid residues of the SP-B protein.

It is contemplated that the polypeptides of this invention may comprise addition analogs (wherein one or more amino acid residues which are not naturally present in a given SP-B sequence are provided in the synthetic polypeptide at terminal or intermediate locations), deletion analogs (wherein one or more residues are deleted from a natural sequence), substitution analogs (wherein one or more residues are replaced by other amino acid residues) and replicate analogs (wherein one or more residues are repeated, replicated, in a natural sequence). Specifically comprehended are interspecies hybrid analogs comprising composite replicas of more than one species (i.e. human, canine, bovine, porcine, etc.) of naturally occurring SP-B proteins and those analogs wherein D-forms of amino acids replace the naturally occurring L-forms. The polypeptides of this invention preferably retain the overall hydrophobic character of the SP-B protein are expected to also retain substantial elements of secondary and tertiary conformation.

As with native SP-B, (complete protein) the polypeptides of this invention are readily formulated with either natural or synthetic phospholipids to yield admixtures which are useful in the treatment of pulmonary surfactant deficient (e.g. hyaline membrane disease) and/or abnormal (e.g. respiratory distress syndrome, RDS) surfactant states, and for pulmonary drug delivery systems. The synthetic fragments of this invention are also expected to have considerable use in the preparation of polyclonal and monoclonal antibodies exhibiting specificity for the antigenic determinants occurring on natural SP-B and which would therefore be useful inter alia in immunopurification and/or quantitative assessment of the SP-B protein in clinical immunodiagnosis.

Other aspects and advantages of the invention will be apparent upon consideration of the following detailed description of the illustrative embodiments hereof.

Experimental

The following examples relate to the synthesis and testing of polypeptides of the invention. More specifically, Examples 1-3 relate to the synthesis of polypeptides patterned on the entire amino acid sequence for the human SP-B protein. Table 1 (supra) sets forth the position, molecular weight and number of amino acids constituting the various synthesized SP-B fragments. All fragments were synthesized, cleaved and purified. Examples 4 and 5 relate to the formulation and testing of polypeptide/phospholipid admixtures. The data illustrate markedly improved surfactant-like activity of the carrier phospholipids when combined with the peptides of this invention.

The compounds of the invention may also be prepared by partial solid phase synthesis, fragment condensation methods and classical solution methods as exemplified by the methods described in "peptide synthesis", second edition, M. Bodansky, Y. S. Klausner and M. A. Ondetti (1976).

Example 1

Synthesis of SP-B(1-78) A molecule having the sequence:

NH₂—Phe—Pro—Ile—Pro—Leu—Pro—Tyr—Cys—Trp—Leu—Cys—Arg—
      1                                       10

Ala—Leu—Ile—Lys—Arg—Ile—Gln—Ala—Met—Ile—Pro—Lys—Gly—Ala—Leu—Arg—Val—Ala—
                 20                                              30

Val—Ala—Gln—Val—Cys—Arg—Val—Val—Pro—Leu—Val—Ala—Gly—Gly—Ile—Cys—Gln—Cys—Leu—
                                       40

Ala—Glu—Arg—Tyr—Ser—Val—Ile—Leu—Leu—Asp—Thr—Leu—Leu—Gly—Arg—Met—Leu—Pro—Gln—
      50                                            60

Leu—Val—Cys—Arg—Leu—Val—Leu—Arg—Cys—Ser—OH
      70                              78 was made so as to provide a replica of the entire 78 amino acid residue sequence of the native human SP-B protein. This polypeptide was assembled on a phenylacetamidomethyl (PAM) resin support by stepwise solid phase synthesis (starting with the carboxyl terminal residue) according to the general procedure described by Barany, G. and Merrifield, R., described in *The Peptides*, Gross, E. and Meinenhofe, J. eds, 2 1-284, Academic Press, New York, N.Y., 1980. The C-terminal amino acid residue, serine (Ser) was coupled to the PAM resin support via an oxymethyl phenylacetamidomethyl (OMPA) linkage owing to the enhanced acid stability of the PAM resin which thereby ensures improved stability during prolonged treatment with trifluoroacetic acid (TFA). Following C-terminal Ser coupling, the resin (0.72 mole /g, 0.70 g) was transferred to the reaction vessel of an Applied Biosystems Peptide Synthesizer model 430A. The next eight amino acids were coupled in a stepwise manner using a preformed symmetric anhydride coupling protocol, except for arginine additions at positions 76 and 72 which were double coupled using N,N-dicyclohexylcarbodiimide (DCC)/-hydroxybenzotriazole (HOBT) chemistry. The synthesis was then continued using the double coupling protocol for all subsequent amino acids. All amino terminal residues were protected by t-butyloxy carbonyl (t-Boc) linkage. In the first coupling, protected amino acids, except for asparagine, glutamine and arginine, were coupled using preformed symmetric anhydrides dissolved in DMF. The symmetric anhydride of an individual amino acid was formed in methylene chloride followed by solvent exchange to DMF before transferring to the reaction vessel of the peptide synthesizer. The second coupling of symmetric anhydride was conducted in methylene chloride. The amino acids glutamine and asparagine were coupled using the DCC/HOBT protocol. After incorporation of methionine at position 65, indole (1% w/v) and ethanediol (0.25% v/v) were added to TFA. This modified solution was employed for all subsequent removals of the $N^\alpha$ Boc protecting groups.

The functional side chains of various amino acid residues were protected by the following groups:

| | |
|---|---|
| Arg-Tos | (Tosyl) |
| Lys-2CLZ | (2-Chlorobenzyloxycarbonyl) |
| Thr, Ser-Bzl | (Benzyl) |
| Tyr-2 BrZ | (2 Bromobenzyloxycarbonyl) |
| Cys-4MeBzl | (4 Methylbenzyl) |
| Asp, Glu-OBzl | (O-Benzyl) |

The amino acids methionine and tryptophan were used without any side chain protection.

A small amount of peptide-resin (0.6 g) was removed after coupling of tyrosine and leucine at position 53 and 27 respectively. The integrity of the assembled peptide sequence on the resin support was verified by solid phase sequencing of the peptide fragments and at the completion of the synthesis on the ABI 470A gas phase sequencer.

The fully protected peptide-resin (330 mg) was allowed to swell in methylene chloride for 5 minutes. The $N^\alpha$-Boc protecting group was cleaved using TFA containing 1% (w/v) indole and 0.1% (v/v) ethanediol as described above. The unblocked swollen peptide-resin was then treated with 11 ml of anhydrous hydrogen fluoride (HF) to which 1 ml p-cresol, 0.2 g p-thiocresol and 1 ml of dimethylsulfide (DMS) had been added for 60 minutes at 0° C. This results in the cleavage of the protein or peptide from the support resin.

The HF/DMS was distilled off in vacuo at 0° C. The cleaved peptide and resin were washed 3 times with 15 ml aliquots of cold diethyl ether, and the free peptide was then extracted by washing three times with 10 ml washes of cold TFA. The wash was immediately filtered, and the crude peptide precipitated by the addition of 120–150 ml ice-cold water. The crude peptide was then collected as a pelleted solid by centrifugation at 1000 g for 30 minutes at 0° C. The pellet was washed with 15 ml of diethyl ether and then centrifuged. This wash procedure was repeated three times with diethyl ether, one time with ethyl acetate and two times with distilled water.

The crude peptide (170 mg yield 82%) was analyzed and purified by reverse-phase high performance liquid chromatography (RPLC) on a C4 column (Vydac, catalog #214-Tp-54) employing 0.1% TFA (A) and 100% acetonitrile (B) as the solvent system. The solvent gradient employed for peptide purification started with 52% B solvent. The column was maintained at 52% B for three minutes followed by an increase over 20 minutes using a linear gradient to 72% B. Finally, the column was brought back to 52% B over a one minute period.

The presence of peptide in the effluent was monitored at 225 nm and 280 nm. The amino acid composition of the purified peptide was determined by acid hydrolysis (12N HCl/TFA (2:1, v/v) containing 5% (v/v) thioglycolic acid at 150° C. for 4 hours in vacuo. After removal of the acid, the hydrolysate was analyzed on a Beckman 6300 amino acid analyzer.

The purified peptide was dissolved in n-propanol and a UV spectrum from 210 nm to 330 nm on a Beckman DB Spectrophotometer was also obtained.

EXAMPLE 2

Synthesis of SP-B (1-20)

Completely protected peptide having the sequence:

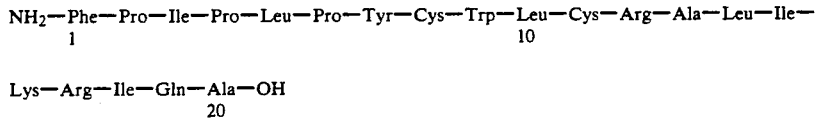

was assembled on a solid support in a manner analogous to the synthesis described in Example 1. HF cleavage from the resin and purification of the cleaved SP-B (1-20) peptide was achieved essentially as described in Example 1. The peptide was cleaved off the resin at 0° C. for one hour using anhydrous HF (9 ml) to which p-cresol (0.5 ml) and thiocresol (0.5 g) had been added. After removal of HF and other volatiles, the cleaved peptide and resin were washed with ether as described above. The peptide was extracted with 1) 3 times 15 ml aliquots of 15% aq. acetic acid; 2) 3 times 40% aq. acetic acid. The combined aqueous extracts were lyophylized to obtain crude peptide. It was purified in a manner analogous to that described in example 1.

EXAMPLE 3

Synthesis of SP-B (53-78)

Completely protected peptide having the sequence:

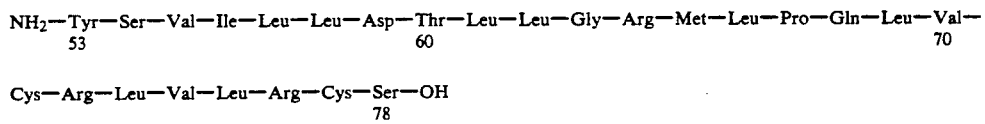

was assembled on a solid support in a manner analogous to the synthesis described in Example 1. HF cleavage from the resin and purification of the cleaved SP-B (53-78) peptide was achieved essentially as described in Example 1 except that ethanedithiol was substituted for thiocresol.

In addition to the fragments described in detail above, the following fragments were also prepared and tested.

The methodology employed was analogous to that described in Example 1.

SP-B (1-40):

NH$_2$—Phe—Pro—Ile—Pro—Leu—Pro—Tyr—Cys—Trp—Leu—Cys—Arg—Ala—Leu—Ile—Lys—Arg—Ile—
1                                                            10

Gln—Ala—Met—Ile—Pro—Lys—Gly—Ala—Leu—Arg—Val—Ala—Val—Ala—Gln—Val—Cys—Arg—Val—Val—
20                                          30

Pro—Leu—OH
40

SP-B (1-60):

NH$_2$—Phe—Pro—Ile—Pro—Leu—Pro—Tyr—Cys—Trp—Leu—Cys—Arg—
1                                                10

Ala—Leu—Ile—Lys—Arg—Ile—Gln—Ala—Met—Ile—Pro—Lys—Gly—Ala—Leu—Arg—Val—Ala
                    20                                      30

Val—Ala—Gln—Val—Cys—Arg—Val—Val—Pro—Leu—Val—Ala—Gly—Gly—Ile—Cys—Gln—Cys—Leu
                                40

Ala—Glu—Arg—Tyr—Ser—Val—Ile—Leu—Leu—Asp—Thr—OH
50                              60

SP-B (12-60):

NH$_2$—Arg—Ala—Leu—Ile—Lys—Arg—Ile—Gln—Ala—Met—Ile—Pro—Lys—Gly—Ala—Leu—Arg—Val—
12                                    20

Ala—Val—Ala—Gln—Val—Cys—Arg—Val—Val—Pro—Leu—Val—Ala—Gly—Gly—Ile—Cys—Gln—Cys—Leu—
30                                          40

Ala—Glu—Arg—Tyr—Ser—Val—Ile—Leu—Leu—Asp—Thr—OH
50                              60

SP-B (40-60):

NH$_2$—Ala—Val—Ala—Gln—Val—Cys—Arg—Val—Val—Pro—Leu—Val—Ala—Gly—Gly—Ile—Cys—Gln—
30                                          40

Cys—Leu—Ala—Glu—Arg—Tyr—Ser—Val—Ile—Leu—Leu—Asp—Thr—OH
       50                                    60

SP-B (27-78):

NH$_2$—Leu—Arg—Val—Ala—Val—Ala—Gln—Val—Cys—Arg—Val—Val—Pro—Leu—Val—Ala—Gly—Gly—
27        30                                            40

Ile—Cys—Gln—Cys—Leu—Ala—Glu—Arg—Tyr—Ser—Val—Ile—Leu—Leu—Asp—Thr—Leu—Leu—Gly—Arg—
                    50                                    60

Met—Leu—Pro—Gln—Leu—Val—Cys—Arg—Leu—Val—Leu—Arg—Cys—Ser—OH
                    70                              78

Tests were conducted to determine the biophysical (surface) activity of admixtures of synthetic phospholipids combined in vitro with each of the purified synthetic peptide fragments either alone or in various fragment combinations.

EXAMPLE 4

Synthetic Peptide Admixture Formulation

Prior to testing for surface activity, the synthetic fragments were admixed with lipids. A lipid mixture consisting of 68% 1,2 dipalmitoylsn-phosphatidylcholine (DPPC), 22% egg phosphatidylglycerol (PG) and 9% palmitic acid on a weight basis was prepared by dissolving the lipids in chloroform:methanol (2:1). The required amount of peptide fragment was dissolved in methanol and heated to 60° C. for 10 minutes and then cooled to 45° C. The peptide solution was then added to the lipid mixture prewarmed to 45° C. Samples were mixed at 45° C. by gentle swirling on a Bucchi rotavap. The organic solvents were then evaporated at 45° C. through the application of a vacuum (600 torr). Following evaporation, the solids were then suspended in 10% ethanol in deionized distilled water with gentle bath sonication. The sonicated suspension was gently mixed for 30 minutes at 45° C. Thereafter, the ethanol was removed through the application of a vacuum (150 torr). Following complete removal of ethanol the suspension was diluted with 0.15M NaCl to yield an admixture with a phospholipid concentration of 25 mg/ml. Following formulation the admixtures were stored at 4° C. for 48 hours prior to testing.

The synthetic peptide fragments were either mixed with the lipids only, or with another peptide fragment shown in Table 1 plus lipids, or with a fragment of the other low molecular weight surfactant protein, SP-C (i.e. synthetic SP-C (1-60) or SP-C (6-41). The synthetic SP-C fragments were prepared in a manner analogous to that described in Example 1 but the amino acid sequence was based on that of natural SP-C.

The peptide/lipid admixtures were formed at final peptide concentrations of 0.5 mg/ml (equivalent to 2% of solids concentration). When more than one peptide was employed in the admixture, the total final peptide concentration was always maintained at 0.5 mg/ml (2% of solids). If two peptides were used then each was used at a final concentration of 0.25 mg/ml.

In order to determine relative surface activity of these admixtures, they were compared to commercially available natural surfactants (Surfactant TA, Abbott Laboratories; Surfacten, Tokyo Tanabe), commercially available synthetic surfactants, (Exosurf, Burroughs-Welcome) and a synthetic lipid admixture standard. The commercially available surfactants were utilized as received. Biophysical testing was assayed using both the modified Wilhelmy balance (Langmuir Trough) system and the pulsating bubble surfactometer (PBS). For clarity these techniques are briefly described below.

Modified Wilhelmy Surface Balance (a) Surface tension versus compressed surface area The dynamic surface tension lowering properties of the peptide/lipid admixtures were studied using a modified Wilhelmy Surface Balance (Langmuir Trough). The instrument consists of an all Teflon trough and movable Teflon ribbon (dam) barrier system which completely contains and defines a variable surface area. Surface area was varied through the use of a constant rate reversible 3-phase motor to drive the Teflon barrier. A Cahn 2000 electrobalance (Cahn Instruments, Cerittos, Calif.) with a sandblasted 1 cm platinum plate and stainless steel hangdown wire was employed to determine the surface tension at the liquid-air interface. The entire apparatus was situated in a thermostated incubator set at 45° C. Surface area-surface tension measurements were made by adding 950 ml of 0.15M NaCl to the trough. Subphase temperature was controlled during the measurements at 36°-38° C.

For each experiment 27 ul of peptide/lipid admixture was applied in a random array of 13 ($\simeq$2 ul) droplets to the surface of the temperature controlled subphase and allowed to spread spontaneously for 3 minutes. (The 27 ul application corresponds to 675 ug of phospholipid). The trough surface area was then cycled from a maximum (445 sq. cm) to a minimum (178 sq. cm) surface area and back to maximum at a cycling rate of 3 cycles/min (compression ratio 2.5:1). The dynamic surface tension vs surface area was recorded for 7 complete compression-expansion cycles for each application.

(b) Absorption Rate

A procedure similar to that described by Notter, et al., *Pediatric Res.* 16, 515-519, (1982) was employed to determine the absorption rate in the absence of diffusion resistance. The modified Wilhelmy surface balance as described above was used. However, instead of using a Langmuir trough a round Teflon dish (5.1 cm diameter) was employed. The subphase, 70 ml of 0.15M NaCl, was allowed to equilibrate to 37° C. in the incubator and was continuously stirred with a Teflon coated magnetic stirer. An aliquot of the peptide/lipid fragment admixture containing 5 mg of total phospholipid was dispersed in 10 ml of 0.15M NaCl by vortexing for 10 seconds. This dispersion was then added to the saline subphase. Surface tension lowering was monitored using a strip chart recorder connected to the electro balance output.

Details of these techniques are as described in Notter, et al., Pediatric Res. 16, 515-519, 1982; Notter et al., Chem Phys. Lipids 33, 67-80, (1983); Egan et al., J. Applied Physiol. 55, 875-883, (1983); Bermel et al., Lung 162, 99-113, (1984); Notter, et al., Pediatric Res. 20, 569-577, (1985); Holm, et al., Chem Phys Lipids 38, 287-298, (1985).

The Pulsating Bubble Surfactometer (PBS). The PBS equipment (Electronetics, Buffalo, N.Y.) used was essentially equivalent to that described in detail by G. Enhorning, J. Appld. Physiol. 43, 198-203, (1977). Recordings were made of the pressure gradient across the wall of a small air bubble, communicating with ambient air by means of a narrow chimney stack, but otherwise entirely surrounded by a 40 ul volume of the peptide/lipid admixture. The admixture concentration employed for these studies was 1 mg/ml total phospholipid (0.02 mg/ml total peptide) and the diluent was 0.15M NaCl. Immediately prior to loading the sample chamber, the diluted samples were sonicated for 15 seconds to remove any gas nuclei.

The pressure drop across the air-water interface was measured during pulsation by a pressure transducer, and the corresponding surface tension determined through the application of Young's law and the Laplace equation. Measurements were all made at 37° C. and the bubble pulsed at 20 cycles/minute to render respectively a maximum (1.1 mm) and a minimum (0.8 mm) bubble diameter. (This compression/expansion corresponds to a 50% change in the surface area of the air-water interface).

Dynamic surface tension and absorption facility are summarized in Tables 2 and 3 below. Table 2 summarizes the dynamic surface tension and adsorption data obtained with the various peptide-lipid admixtures on the Wilhelmy Balance-Langmuir Trough System. To one skilled in the art, it is obvious that low minimum dynamic surface tension values and reduced adsorption surface tension values are desirable properties of a good surfactant formulation.

TABLE 2

Dynamic Surface Tension and Adsorption Capacity of Synthetic Peptide Fragment Admixtures as determined by the Modified Wilhelmy Balance-Langmuir Trough System.

| Sample | Surface Tension[a] (dynes/cm) Maximum | Surface Tension[a] (dynes/cm) Minimum | Adsorption (dynes/cm) |
|---|---|---|---|
| (a) Controls | | | |
| Surfactant-TA | 39.0 | 7.5 | 33.5 |
| Surfacten | 51.5 | 2.5 | 26.0 |
| Exosurf (No protein) | 63.0 | 12.0 | 58.0 |
| Tanaka Lipids (No protein) | 61.0 | 16.01 | 60.0 |
| (b). Peptide Fragment[b] | | | |
| 1. One-Peptide Fragment | | | |
| SP-B(1-78) | 44.0 | <1 | 37.5 |
| SP-B(1-20) | 52.5 | <1 | 49.5 |
| SP-B(1-40) | 48.5 | <1 | 42.5 |
| SP-B(1-60) | 47.5 | <1 | 42.0 |
| SP-B(12-60) | 49.0 | <1 | 41.0 |
| SP-B(30-60) | 52.0 | <1 | 41.0 |
| SP-B(27-78) | 49.5 | <1 | 40.0 |
| SP-B(53-78) | 47.5 | <1 | 42.5 |
| 2. Two Peptide Admixtures[c] | | | |
| SP-B(1-20) + SP-B(53-78) | 47.5 | <1 | 42.5 |
| SP-B(1-40) + SP-B(53-78) | 48.0 | <1 | 42.5 |
| SP-B(1-40) + SP-B(53-78) | 48.0 | <1 | 41.5 |
| SP-B(1-20) + SP-C(1-60) | 48.0 | <1 | 41.5 |
| SP-B(1-20) + SP-C(6-41) | 47.5 | <1 | 36.5 |
| SP-B(53-78) + SP-C(1-60) | 52.5 | 5.0 | 45.0 |
| SP-B(53-78) + SP-C(6-41) | 45.0 | <1 | 38.0 |
| SP-B(1-78) + SP-C(1-60) | 54.0 | <1 | 42.5 |

TABLE 2-continued

Dynamic Surface Tension and Adsorption Capacity of Synthetic Peptide Fragment Admixtures as determined by the Modified Wilhelmy Balance-Langmuir Trough System.

| Sample | Surface Tension[a] (dynes/cm) Maximum | Minimum | Adsorption (dynes/cm) |
|---|---|---|---|
| SP-B(1-78) + SP-C(6-41) | 47.5 | <1 | 36.0 |

[a]Minimum/Maximum values recorded during seven complete cycles. In all cases 675 ug of phospholipid was added to the Langmuir Trough at maximum dimensions of 445 sq. cm.
[b]Peptide concentration is 0.5 mg/ml (≈2% of solids).
[c]Total peptide concentration is 0.5 mg/ml (2.0% of solids); each peptide concentration is 0.25 mg/ml.

From the data contained in Table 2 above, it is clear that each of the synthetic SP-B fragment admixtures either alone or in combination with another SP-B fragment or SP-C peptide significantly reduces the minimum dynamic surface tension to an extent that is comparable or better than that exhibited by natural surfactant (e.g. Surfactant-TA). With one exception only, all of the Peptide Fragment and Two Peptide Admixtures yield a dynamic surface tension value of less than 1 dyne/cm whereas natural surfactant (e.g. Surfactant-TA) yields a minimum dynamic surface tension of about 8 dynes/cm.

Table 3 summarizes the minimum surface tension values at the air-aqueous interface obtained for the various peptide-admixtures on the pulsating bubble surfactometer. As with the Wilhelmy Balance, to one skilled in the art it will be obvious that low surface tension values are a desirable property of a good surfactant admixture.

TABLE 3

Surface tension values obtained via the Pulsating Bubble Surfactometer after 5 minutes pulsation (100 cycles).

| Sample[a] | Minimum Surface Tension[b] (dyne/cm) |
|---|---|
| a. Controls | |
| Surfactant-TA | 4.6 ± 0.41 |
| Surfacten | 4.7 ± 0.21 |
| Exosurf | 29.8 ± 0.01 |
| Tanaka Lipids | 23.5 ± 0.01 |
| b. Peptide Admixture[c] | |
| SP-B(1-20) | 3.4 ± 0.68 |
| SP-B(1-40) | 7.1 ± 0.41 |
| SP-B(1-60) | 7.2 ± 0.26 |
| SP-B(1-78) | 4.0 ± 0.72 |
| SP-B(12-60) | 10.3 ± 0.67 |
| SP-B(30-60) | 16.9 ± 0.95 |
| SP-B(27-78) | 4.7 ± 0.26 |
| SP-B(53-78) | 1.5 ± 0.63 |

[a]All samples run at a concentration of 1 mg/ml phospholipid; diluent employed was 0.15M NaCl in glass distilled deionized water; temperature = 37° C., and a pulsation cycle of 20 cycles/minute.
[b]Values reported are those obtained after 5 minute pulsation time, i.e. after 100 pulsations.
[c]Total peptide concentration in all cases is 2% of phospholipids (0.5 mg/ml).

It is clear from the data contained in Table 3 that each of the SP-B fragments examined significantly enhances the surface tension lowering capacity of the carrier lipids. Further, it is also clear that fragments containing a terminal amino acid sequence, especially the two fragments SP-B (1-20) and SP-B (53-78) are particularly effective in their ability to facilitate low surface tension values. This finding is both unexpected and surprising, and forms in part, the basis of this invention.

The data contained in both Tables 2 and 3, as evidenced by the minimum surface tension values, demonstrates that admixtures of phospholipid and peptide fragment of this invention exhibit markedly improved surface activity as compared to admixtures containing synthetic lipids only and are comparable to the two commercial formulations Surfactant-TA and Surfacten. The two terminal peptide fragments SP-B (1-20) and SP-B (53-78) are particularly effective in surface tension lowering capacity.

EXAMPLE 5

As shown in Tables 2 and 3, all of the peptide fragments shown in Table 1 either alone or in various combinations are able to significantly lower the minimum surface tension of the carrier lipids. Thus in order to determine which of the various fragments exhibited superior activity and to further define the relative surface activity of the various peptide fragments (admixed with the standard lipid mixture described in Example 4), the peptide concentration of 0.5 mg/ml (2% of solids) was reduced in order to establish (on the modified Wilhelmy surface balance) the lowest peptide concentration which exhibited surface activity. For the purpose of this comparison "surface activity" is defined as follows: For any given peptide concentration, the admixture is required to result in a minimum dynamic surface tension of less than 5 dynes/cm for each of seven consecutive expansion/compression cycles.

The admixtures were diluted with the synthetic lipid mixture as described in Example 4, so as to maintain the lipid concentration in all cases at 25 mg/ml. For these studies a standard volume of 27 ul, corresponding to a total phospholipid mass of 675 ug, was applied to the Langmuir Trough with maximum dimensions of 445 sq. cm. The results of this study are shown below in Table 4.

For the purpose of interpreting the data contained in Table 4, it should be recognized that the more effective (i.e. surface active) SP-B fragments will meet the designated criteria at lower peptide concentrations, i.e. the lower the peptide concentration that is required in order to meet the designated surface activity criterion, the more surface active is that peptide fragment. Table 4 does not list data for the lipid control since no protein (peptide) is contained therein.

TABLE 4

Relative Surface Activity of Single Peptide Admixtures as determined by dilution studies performed on the modified Wilhelmy Balance-Langmuir Trough.

| Sample[a] | Lowest Peptide (Protein) Concentration At Which Surface Active Criteria[b] Are Met. | |
|---|---|---|
| | ug/ml | uM |
| 1. Controls | | |
| Surfactant-TA | 250 | — |
| Surfactant | 250 | — |
| 2. Synthetic Peptide Analogs | | |
| SP-B(1-20) | 5.0 | 1.9 |
| SP-B(1-40) | 15.0 | 3.3 |
| SP-B(1-60) | 125.0 | 18.9 |
| SP-B(1-78) | 15.0 | 1.7 |
| SP-B(12-60) | 30.0 | 11.4 |
| SP-B(30-60) | 250.0 | 76.7 |
| SP-B(27-78) | 30.0 | 5.3 |
| SP-B(53-78) | 3.5 | 1.2 |

[a]In all cases 675 ug phospholipid was applied to the Langmuir Trough at maximum expansion (445 sq. cm). Peptide samples were diluted with lipid admixture so as to retain phospholipid concentration at 25 mg/ml in all cases. Subphase was 0.15M NaCl in glass distilled deionized water.
[b]For any given peptide concentration, the admixture is required to result in a minimum dynamic surface tension of less than 5 dynes/cm for each of seven consecutive expansion/compression cycles.

The data contained in Table 4 clearly demonstrates that the various peptide fragments exhibit varying and different degrees of surface activity as determined by these dilution studies. It is particularly surprising that the carboxyl and amino-terminal containing fragments SP-B(1-20) and SP-B(53-78) exhibit biophysical surface activity equivalent to or better than that exhibited by the entire SP-B protein sequence, i.e. SP-B(1-78).

It is clear from the data contained in Tables 3 and 4 that the SP-B peptide fragments according to this invention, produce markedly enhanced surface activity as compared to synthetic lipids alone or synthetic lipids plus other peptide fragments. The unusual surface activity exhibited by the two terminal fragments SP-B (1-20) and SP-B(53-78) is both surprising and unexpected.

Industrial Applicability

This invention overcomes numerous problems associated with natural, synthetic or recombinant SP-B (1-78). It is quite apparent that production of only the C- and/or N-terminus of the SP-B (1-78) molecule will enhance and accelerate the commercial production of pulmonary surfactant products.

The foregoing detailed description is given for clearness of understanding only, and no unnecessary limitation should be understood therefrom, as modifications will be obvious to those skilled in the art.

We claim:

1. A composition of matter which comprises a fragment of the SP-B protein which exhibits surfactant activity when admixed with lipids in a weight ratio of said peptide to said lipid of not less than 1:5,000, said SP-B fragment consisting essentially of the amino acid sequence:

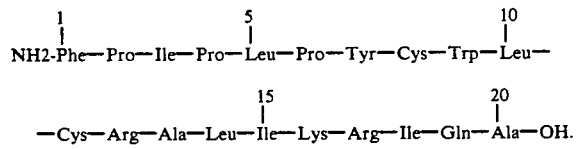

2. A composition of matter characterized by a mixture of the composition according to claim 1 and at least one lipid.

3. A composition of matter according to claim 2 wherein the lipid is selected from the group consisting of synthetic phospholipids, naturally occurring phospholipids, neutral lipids, cholesterol, cholesterol esters, phosphatidylcholine, disaturated phosphatidylcholine, phosphatidylglycerol, dipalmitoyl phosphatidylcholine, phosphatidylinositol and mixtures thereof.

4. A method for treating hyaline membrane disease or other syndromes caused by having insufficient or abnormal surfactant material, said method comprising administration of an effective amount of a surfactant composition to a patient in need of treatment, said surfactant composition comprising the SP-B fragment admixed with lipids in a weight ratio of said peptide to said lipid of not less than 1:5,000, said SP-B fragment consisting essentially of the amino acid sequence:

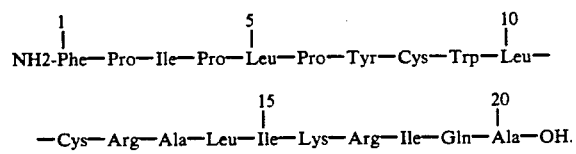

5. The method according to claim 4 wherein said lipid is selected from the group consisting of synthetic phospholipids, naturally occurring phospholipids, neutral lipids, cholesterol, cholesterol esters, phosphatidylcholine, disaturated phosphatidylcholine, phosphatidylglycerol, dipalmitoyl phosphatidylcholine, phosphatidylinositol and mixtures thereof.

6. The method as recited in claim 5 wherein said composition is administered to the patient as a liquid or as an aerosol spray.

7. A method for pulmonary drug delivery, said method consisting of administering to a patient in need of said drug therapy, a therapeutically effective amount of a composition comprising: 1) the SP-B protein fragment admixed with 2) lipids in a weight ratio of said peptide to said lipid of not less than 1:5,000, and 3) an appropriate therapeutic agent, said SP-B fragment consisting essentially of the amino acid sequence:

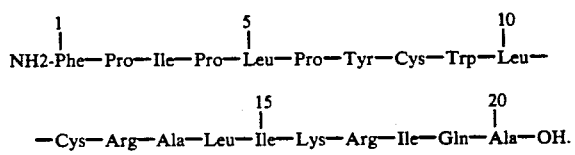

8. A method according to claim 7 wherein the lipid is selected from the group consisting of synthetic phospholipids, naturally occurring phospholipids, neutral lipids, cholesterol, cholesterol esters, phosphatidylcholine, disaturated phosphatidylcholine, phosphatidylglycerol, dipalmitoyl phosphatidylcholine, phosphatidylinositol and mixtures thereof.

9. The method as recited in claim 8 wherein said composition is administered to the patient as a liquid or as an aerosol spray.

10. A composition of matter which comprises a fragment of the SP-B protein which exhibits surfactant activity when admixed with lipids wherein said peptide comprises not less than 200 parts per million of said peptide-lipid composition, said SP-B fragment consisting essentially of the amino acid sequence:

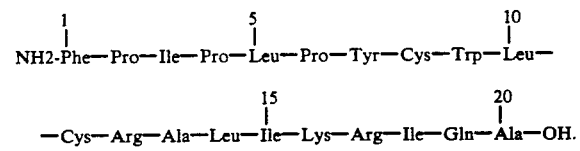

11. A composition of matter characterized by a mixture of the composition according to claim 10 and at least one lipid.

12. A composition of matter according to claim 11 wherein the lipid is selected from the group consisting of synthetic phospholipids, naturally occurring phospholipids, neutral lipids, cholesterol, cholesterol esters, phosphatidylcholine, disaturated phosphatidylcholine, phosphatidylglycerol, dipalmitoyl phosphatidylcholine, phosphatidylinositol and mixtures thereof.

13. A method for treating hyaline membrane disease or other syndromes caused by having insufficient or abnormal surfactant material, said method comprising administration of an effective amount of a surfactant composition to a patient in need of treatment, said surfactant composition comprising the SP-B fragment admixed with lipids wherein said peptide comprises not less than 200 parts per million of said peptide-lipid composition, said SP-B fragment consisting essentially of the amino acid sequence:

```
   1                   5                      10
   |                   |                      |
NH2-Phe—Pro—Ile—Pro—Leu—Pro—Tyr—Cys—Trp—Leu—
                       15                     20
                       |                      |
   —Cys—Arg—Ala—Leu—Ile—Lys—Arg—Ile—Gln—Ala—OH.
```

14. The method according to claim 13 wherein said lipid is selected from the group consisting of synthetic phospholipids, naturally occurring phospholipids, neutral lipids, cholesterol, cholesterol esters, phosphatidylcholine, disaturated phosphatidylcholine, phosphatidylglycerol, dipalmitoyl phosphatidylcholine, phosphatidylinositol and mixtures thereof.

15. The method as recited in claim 14 wherein said composition is administered to the patient as a liquid or as an aerosol spray.

16. A method for pulmonary drug delivery, said method consisting of administering to a patient in need of said drug therapy, a therapeutically effective amount of a composition comprising: 1) the SP-B protein fragment admixed with 2) lipids in a weight ratio of said peptide comprises not less than 200 parts per million of said protein-lipid composition; and 3) an appropriate therapeutic agent, said SP-B fragment consisting essentially of the amino acid sequence:

```
   1                   5                      10
   |                   |                      |
NH2-Phe—Pro—Ile—Pro—Leu—Pro—Tyr—Cys—Trp—Leu—
                       15                     20
                       |                      |
   —Cys—Arg—Ala—Leu—Ile—Lys—Arg—Ile—Gln—Ala—OH.
```

17. A method according to claim 16 wherein the lipid is selected from the group consisting of synthetic phospholipids, naturally occurring phospholipids, neutral lipids, cholesterol, cholesterol esters, phosphatidylcholine, disaturated phosphatidylcholine, phosphatidylglycerol, dipalmitoyl phosphatidylcholine, phosphatidylinositol and mixtures thereof.

18. The method as recited in claim 17 wherein said composition is administered to the patient as a liquid or as an aerosol spray.

* * * * *